(12) United States Patent
Robertson et al.

(10) Patent No.: US 9,034,613 B2
(45) Date of Patent: May 19, 2015

(54) PROCESS FOR THE PREPARATION OF (3R)-HYDROXYBUTYL (3R)-HYDROXYBUTYRATE BY ENZYMATIC ENANTIOSELECTIVE REDUCTION EMPLOYING *LACTOBACILLUS BREVIS* ALCOHOL DEHYDROGENASE

(75) Inventors: Jeremy Robertson, Oxford (GB); Kieran Clarke, Oxford (GB); Richard Lewis Veech, Rockville, MD (US)

(73) Assignees: ISIS Innovation Limited, Rockville Maryland; The United States of America, as Represented by the Secretary, Department of Health & Human Services, Washington, DC (US)

( * ) Notice: Subject to any disclaimer, the term of this patent is extended or adjusted under 35 U.S.C. 154(b) by 850 days.

(21) Appl. No.: 13/264,533

(22) PCT Filed: Apr. 16, 2009

(86) PCT No.: PCT/US2009/040773
§ 371 (c)(1),
(2), (4) Date: Oct. 14, 2011

(87) PCT Pub. No.: WO2010/120300
PCT Pub. Date: Oct. 21, 2010

(65) Prior Publication Data
US 2012/0064611 A1    Mar. 15, 2012

(51) Int. Cl.
*C12P 7/62* (2006.01)
*C12P 41/00* (2006.01)
*C12N 9/02* (2006.01)

(52) U.S. Cl.
CPC ............... *C12P 7/62* (2013.01); *C12P 41/002* (2013.01); *C12N 9/0008* (2013.01)

(58) Field of Classification Search
CPC ........ C12P 7/62; C12P 41/002; C12N 9/0008
USPC .................................. 435/135, 155, 280, 189
See application file for complete search history.

(56) References Cited

FOREIGN PATENT DOCUMENTS

EP          1568780 A1    8/2005
WO    WO2004108740 A2   12/2004

OTHER PUBLICATIONS

Kalaitzakis et al. Org. Lett. (2005) 7(22): 4799-4801.*
Zhu et al. Tetrahedron (2006) 62: 901-905.*
Edegger et al. Eur. J. Org. Chem. (2006) pp. 1904-1909.*
Desrochers, S. et al., "R, S-1, 3-butanediol acetoacetate esters, potential alternates to lipid emulsions for total parenteral nutrition", Journal of Nutritional Biochemistry, vol. 6, Issue 2, Feb. 1995, pp. 111-118.
PCT—International Preliminary Report on Patentability and Written Opinion of the International Searching Authority for PCT/US2009/040773 dated Oct. 18, 2011.
PCT—International Search Report for PCT/US2009/040773 dated Feb. 22, 2010.

* cited by examiner

*Primary Examiner* — Susan Hanley
(74) *Attorney, Agent, or Firm* — Lathrop & Gage LLP; Brian C. Trinque

(57) ABSTRACT

A process for producing a compound which is (3R)-hydroxybutyl (3R)-hydroxybutyrate of formula (I) which process comprises submitting, to enantioselective reduction, a compound of the following formula (II), (III) or (IV).

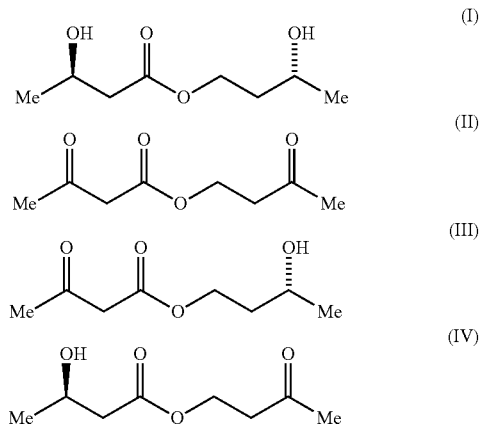

17 Claims, No Drawings

PROCESS FOR THE PREPARATION OF (3R)-HYDROXYBUTYL (3R)-HYDROXYBUTYRATE BY ENZYMATIC ENANTIOSELECTIVE REDUCTION EMPLOYING LACTOBACILLUS BREVIS ALCOHOL DEHYDROGENASE

STATEMENT REGARDING FEDERALLY SPONSORED RESEARCH OR DEVELOPMENT

This invention was made with government support under Grant No. W911NF-05-1-0479 awarded by ARMY/ARO. The U.S. Government has certain rights in the invention.

CROSS-REFERENCE TO RELATED APPLICATIONS

This is a U.S. National Stage Application of International Application No. PCT/US2009/040773, filed on Apr. 16, 2009, the disclosure of which is hereby incorporated herein by reference in its entirety.

FIELD OF THE INVENTION

The present invention relates to the synthesis of 3-hydroxybutyl 3-hydroxybutyrate in enantiomerically enriched form.

BACKGROUND OF THE INVENTION

Ketone bodies are chemical compounds which are produced when fatty acids are metabolised by the body for energy. Ketone bodies themselves can also be used for energy.

The intake of compounds that boost the levels of ketone bodies in the blood can lead to various clinical benefits, including an enhancement of physical and cognitive performance. As disclosed in WO 2004/108740, 3-hydroxybutyl 3-hydroxybutyrate is an example of such a compound that can be administered as a food additive.

3-Hydroxybutyl 3-hydroxybutyrate possesses two stereogenic centres in its structure, which means that there are four distinct stereoisomers of the compound: two diastereoisomers, both consisting of a pair of enantiomers. Published syntheses of this compound produce a mixture of all four stereoisomers but, of these four, the (3R,3'R) isomer is the most effective precursor of (3R)-hydroxybutyrate ('D-3-hydroxybutyrate'), an important member of the ketone bodies biosynthesised and utilised in vivo. A convenient means of producing this compound in enantiomerically enriched form is therefore required.

In addition to the general routes disclosed in WO 2004/108740, various synthetic approaches have been developed for the production of the desired stereoisomer. As a benchmark, a classical synthesis, from poly[(3R)-hydroxybutyric acid], gives pure product but involves six chemical steps. Other synthetic strategies have various technical drawbacks including low yields, the production of impure product, or impracticability on a large scale.

SUMMARY OF THE INVENTION

The present inventor has devised a synthetic route to (3R)-hydroxybutyl (3R)-hydroxybutyrate which is short and which is capable of operation on a manufacturing scale. Accordingly, the present invention provides a process for producing (3R)-hydroxybutyl (3R)-hydroxybutyrate of formula (I):

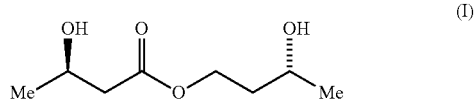 [SMILES: C[C@@H](O)CCOC(=O)C[C@@H](C)O]

which process comprises submitting, to enantioselective reduction, a compound of the following formula (II), (III) or (IV):

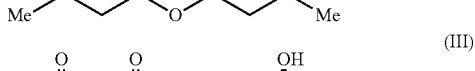

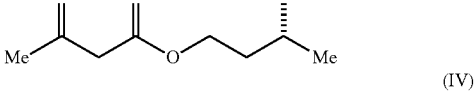

More typically, the process comprises submitting, to enantioselective reduction, a compound of formula (II) or (III) as defined above.

The invention further provides a process for producing (3R)-hydroxybutyl (3R)-hydroxybutyrate of formula (I):

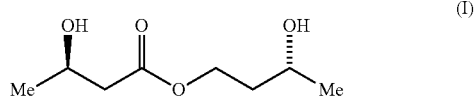 [SMILES: C[C@@H](O)CCOC(=O)C[C@@H](C)O]

which process comprises:
(a) treating 4-hydroxybutan-2-one of formula (V)

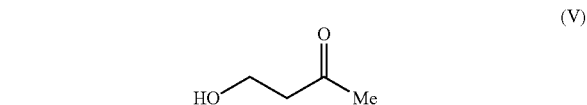

with diketene of formula (VI)

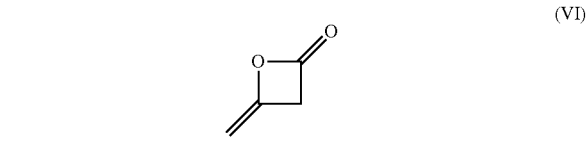

to produce a compound of formula (II):

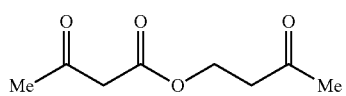

(II)

and (b) submitting the compound of formula (II) to enantioselective reduction.

Still further, the invention provides a process for producing (3R)-hydroxybutyl (3R)-hydroxybutyrate of formula (I):

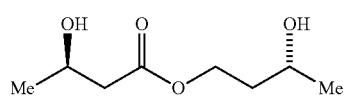

(I)

which process comprises:

(a) treating 4-hydroxybutan-2-one of formula (V):

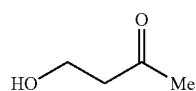

(V)

with 2,2,6-trimethyl-4H-1,3-dioxin-4-one of formula (IX):

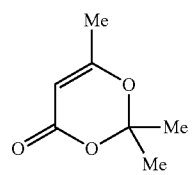

(IX)

in the presence of a transesterification reagent to produce a compound of formula (II):

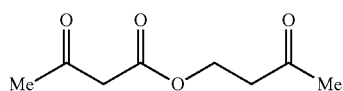

(II)

and (b) submitting the compound of formula (II) to enantioselective reduction.

Still further, the invention provides a process for producing (3R)-hydroxybutyl (3R)-hydroxybutyrate of formula (I):

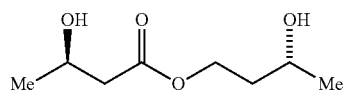

(I)

which process comprises:

(a) treating 4-hydroxybutan-2-one of formula (V):

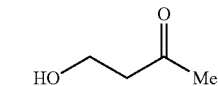

(V)

with a compound of formula (X):

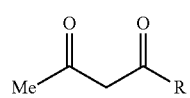

(X)

wherein R is halo or —OR$^1$, wherein R$^1$ is selected from hydrogen, unsubstituted or substituted C$_{1-6}$ alkyl and —C(O)R$^2$ wherein R$^2$ is unsubstituted or substituted C$_{1-6}$ alkyl or -alk-C(O)—R$^3$ wherein alk is unsubstituted or substituted C$_{1-4}$ alkylene and R$^3$ is unsubstituted or substituted C$_{1-4}$ alkyl, in the presence of an esterification reagent when R is —OR$^1$ and R$^1$ is hydrogen, or in the presence of a transesterification reagent when R is —OR$^1$ and R$^1$ is unsubstituted or substituted C$_{1-6}$ alkyl, to produce a compound of formula (II):

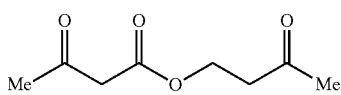

(II)

and (b) submitting the compound of formula (II) to enantioselective reduction.

Still further, the invention provides a process for producing (3R)-hydroxybutyl (3R)-hydroxybutyrate of formula (I):

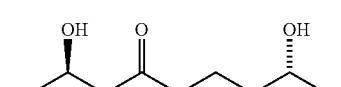

(I)

which process comprises:

(a) treating (R)-1,3-butanediol of formula (VII)

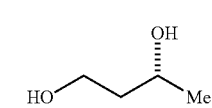

(VII)

with diketene of formula (VI)

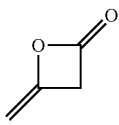
(VI)

and isolating a compound of formula (III) from the resulting mixture of acylated products:

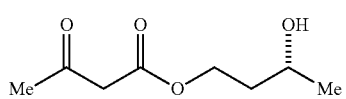
(III)

and (b) submitting the compound of formula (III) to enantioselective reduction.

Still further, the invention provides a process for producing (3R)-hydroxybutyl (3R)-hydroxybutyrate of formula (I):

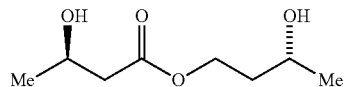
(I)

which process comprises:

(a) treating (R)-1,3-butanediol of formula (VII):

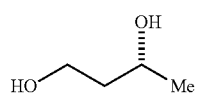
(VII)

with 2,2,6-trimethyl-4H-1,3-dioxin-4-one of formula (IX):

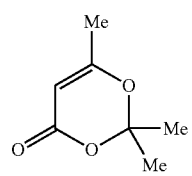
(IX)

in the presence of a transesterification reagent, to produce a compound of formula (III):

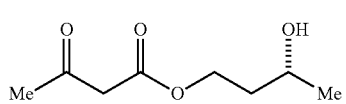
(III)

and (b) submitting the compound of formula (III) to enantioselective reduction.

Still further, the invention provides a process for producing (3R)-hydroxybutyl (3R)-hydroxybutyrate of formula (I):

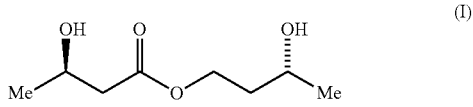 [SMILES: C[C@@H](O)CCOC(=O)C[C@@H](C)O]
(I)

which process comprises:

(a) treating (R)-1,3-butanediol of formula (VII):

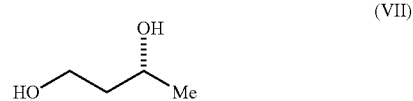
(VII)

with a compound of formula (X):

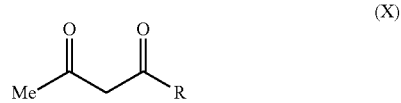
(X)

wherein R is halo or —OR$^1$, wherein R$^1$ is selected from hydrogen, unsubstituted or substituted C$_{1-6}$ alkyl and —C(O)R$^2$ wherein R$^2$ is unsubstituted or substituted C$_{1-6}$ alkyl or -alk-C(O)—R$^3$ wherein alk is unsubstituted or substituted C$_{1-4}$ alkylene and. R$^3$ is unsubstituted or substituted C$_{1-4}$ alkyl, in the presence of an esterification reagent when R is —OR$^1$ and R$^1$ is hydrogen, or in the presence of a transesterification reagent when R is —OR$^1$ and R$^1$ is unsubstituted or substituted C$_{1-6}$ alkyl, to produce a compound of formula (Ill):

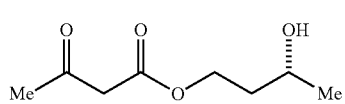
(III)

and submitting the compound of formula (III) to enantioselective reduction.

Still further, the invention provides a process for producing (3R)-hydroxybutyl (3R)-hydroxybutyrate of formula (I):

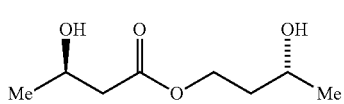
(I)

which comprises:
(a) treating 4-hydroxybutan-2-one of formula (V):

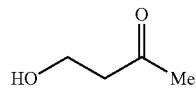
(V)

with (R)-4-methyloxetan-2-one of formula (VIII):

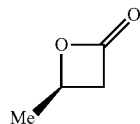
(VIII)

to produce a compound of formula (IV):

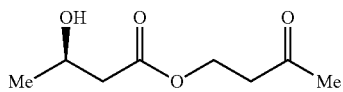
(IV)

and
(b) submitting the compound of formula (IV) to enantioselective reduction.

DETAILED DESCRIPTION OF THE INVENTION

The step of reducing the compound of formula (II), (III) or (IV) can be mediated by an enzyme; for example, a ketoreductase (KRED) or an alcohol dehydrogenase (ADH). This has the advantages of convenience, scalability and non-toxicity, and it is environmentally non-hazardous. The enzyme may be one that is naturally occurring, or commercially available, or one that has been genetically engineered for the purpose.

In the case of compound (II), the reduction is a double asymmetric reduction; that is, of two chemically distinct carbonyl groups, one being the ketone carbonyl in a β-ketoester, the other being the ketone carbonyl in a β-(acyloxy)ketone. This may be achieved using either a single enzyme, typically but not necessarily one that is specifically engineered for the purpose, or two enzymes working either separately or in the presence of one another.

Any suitable enzyme may be used for mediating the reduction of the compound of formula (II), (III) or (IV). Typically, however, the enzyme or enzymes are ketoreductases or alcohol dehydrogenases. Key criteria for selection of a suitable enzyme are as follows:
  1. Commercial availability;
  2. R-enantiomer selectivity;
  3. High activity; and
  4. Ability of the enzyme to function on a support (for ease of product purification).

Typically, the enzyme or enzymes used are commercially available ones. Suitable ketoreductase and alcohol dehydrogenase enzymes are commercially available from various companies; such enzymes were for instance available from Julich Fine Chemicals, Germany, and Biocatalytics, Inc., Pasadena, Calif., USA, both of which are now part of Codexis, Inc., Redwood City, Calif., USA. Potentially suitable ketoreductase enzymes were listed in the Biocatalytics, Inc. catalogue as KRED-### (where ### is a number designation), whereas the alcohol dehydrogenase enzymes available from Julich were designated ADH-XX, where XX refers to the organism from which the enzyme was originally discovered. ADH-LB, for example, is the alcohol dehydrogenase from *Lactobacillus brevis*. Many of these commercially available enzymes are described in a review article by Moore et al., on the enzymatic reduction of ketones (*Acc. Chem. Res.* 2007, 40, 1412-1419).

In order to achieve enantioselective reduction of the compound of formula (II), (III) or (IV) to produce (3R)-hydroxybutyl(3R)-hydroxybutyrate of formula (I), the enzyme or enzymes must have R-enantiomer selectivity. Thus, the enzyme or enzymes must be capable of reducing the compound of formula (II), (III) or (IV), as the case may be, to produce 3-hydroxybutyl 3-hydroxybutyrate which is enriched with respect to the (3R,3'R) enantiomer. The term "enriched", as employed herein, means that the level of the enriching isomer is higher than the level at which that isomer would be present in a racemic mixture. Where a percentage enrichment is referred to, the enriching isomer constitutes that molar percentage of the total 3-hydroxybutyl 3-hydroxybutyrate product present.

The most reliable method for measuring enantiomeric purity is chiral high performance liquid chromatography (chiral HPLC). Measurements are typically made against the corresponding racemic mixture. Alternatively, chiral gas chromatography (chiral. GC) may be used reliably. Accordingly, where a percentage enrichment is referred to herein, the percentage enrichment is typically that measured by chiral HPLC or by chiral GC. Preferably, the percentage enrichment is that measured by chiral HPLC.

Usually, the enzyme employed is one which is capable of reducing said compound of formula (II), (III) or (IV) to produce 3-hydroxybutyl 3-hydroxybutyrate which is enantiomerically enriched to at least 95%, for instance to at least 97%, to at least 98%, or to at least 99%, with respect to (3R)-hydroxybutyl(3R)-hydroxybutyrate.

In the case of formula (II), when only one enzyme is used to perform the double asymmetric reduction, the enzyme is typically one which is capable of reducing said compound of formula (II) to produce 3-hydroxybutyl 3-hydroxybutyrate which is enantiomerically enriched to at least 95%, for instance to at least 97%, to at least 98%, or to at least 99%, with respect to (3R)-hydroxybutyl (3R)-hydroxybutyrate.

Where two different enzymes are used, i.e. a first enzyme for reducing the ketone carbonyl in the β-keto ester moiety of formula (II) and a second enzyme for reducing the ketone carbonyl in the β-(acyloxy)ketone moiety, both enzymes must have R-enantiomer selectivity. Typically, the first and second enzymes are enzymes which, when used in combination to perform the double asymmetric reduction (either separately or in the presence of one another), are together capable of reducing the compound of formula (II) to produce 3-hydroxybutyl 3-hydroxybutyrate which is enantiomerically enriched to at least 95%, for instance to at least 97%, to at least 98%, or to at least 99%, with respect to (3R)-hydroxybutyl (3R)-hydroxybutyrate.

Ketoreductase and alcohol dehydrogenase enzymes which generally have R-enantiomer selectivity are known in the art. For instance, the review article by Moore et al. (*Acc. Chem. Res.* 2007, 40, 1412-1419) lists many R-enantiomer-selective enzymes, including the commercially-available ketoreductases KRED-101, KRED-107, KRED-111, KRED-112, FRED-113, KRED-119, KRED-121, KRED-128, KRED-129, KRED-131, KRED-A1 n and KRED-A1x (see Tables 1 to 3 of *Acc. Chem. Res.* 2007, 40, 1412-1419). Furthermore, the same review indicates that KRED-101 and KRED-107 showed high ee values for converting ethyl acetoacetate into the corresponding R-enantiomer alcohol as shown in Scheme 1 below:

Scheme 1

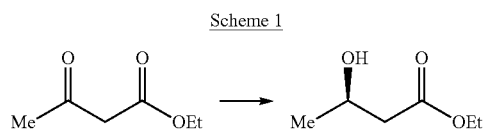

The review article also indicates that the alcohol dehydrogenases ADH-LB and ADH-LK (the alcohol dehydrogenase from *Lactobacillus kefir*) and the ketoreductases KRED-101, KRED-111 to -115, KRED-121 and KRED-123 consistently generate R-enantiomers.

Accordingly, in one embodiment, the enantioselective reduction of the compound of formula (II), (III) or (IV) is carried out using a ketoreductase enzyme selected from: KRED-101, KRED-107, KRED-111, KRED-112, KRED-113, KRED-114, KRED-115, KRED-119, KRED-121, KRED-123, KRED-128, KRED-129, KRED-131, KRED-A1n and KRED-A1x.

In another embodiment, the enantioselective reduction of the compound of formula (II), (III) or (IV) is carried out using an alcohol dehydrogenase enzyme selected from ADH-LB and ADH-LK. More typically, the enantioselective reduction is carried out using ADH-LB.

In the case of formula (II), the enantioselective reduction may be carried out in the presence of two different enzymes, each one being either a ketoreductase enzyme or an alcohol dehydrogenase enzyme. The (or each) ketoreductase enzyme may be selected from KRED-101, KRED-107, KRED-111, KRED-112, KRED-113, KRED-114, KRED-115, KRED-119, KRED-121, KRED-123, KRED-128, KRED-129, KRED-131, KRED-n and KRED-A1x. The (or each) alcohol dehydrogenase enzyme may be selected from ADH-LB and ADH-LK.

More typically, the enantioselective reduction of the compound of formula (II), (III) or (IV) is carried out using ADH-LB.

The activity of the enzyme towards the compound (substrate) of formula (II), (III) or (IV) is desirably as high as possible. The activity of the enzyme towards the substrate may be expressed in terms of the enzyme unit, U, which is the amount of substrate converted, in µmol, per minute. Thus, the enzyme is typically selected such that the activity, expressed in terms of U, is as high as possible. Typically, the activity of the enzyme towards the compound of formula (II), (III) or (IV) is at least 0.1 U/mL, more typically at least 10 U/mL, at least 100 U/mL, at least 200 U/mL or at least 500 U/mL. In one embodiment, the activity is from 0.1 to 825 U/mL, more typically from 10 to 825 U/mL, from 100 to 825 U/mL, from 200 to 825 U/mL or, for instance, from 500 to 825 U/mL.

When the enantioselective reduction of the compound of formula (II), (III) or (IV) is carried out using an enzyme, the enzyme may be unsupported, or supported on a carrier.

In one embodiment, the enzyme is supported on a carrier, typically a solid state carrier. The use of a carrier facilitates separation of the reaction product from the enzyme. Such carriers are well known in the art. The carrier may be an inorganic material, for instance a zeolite, or an organic material, for example a natural or a synthetic polymer. The carrier may be in particulate form or in the form of a membrane or matrix. In one embodiment, the carrier is a conjugated organic polymer. Specific examples of suitable enzyme supports include alginate beads, for instance calcium alginate beads; glass; resin and silica.

In one embodiment, the enzyme is part of a cross-linked enzyme aggregate. Such an aggregate may be formed by linking multiple copies of an enzyme together using a cross linking reagent. The enzymes may be joined together using, for instance, ammonium sulphate or poly(ethylene glycol) as the cross linking reagent.

Directed enzyme evolution is a powerful tool which can be used to optimise the performance of an enzyme. It can be used to improve properties such as enzyme activity, stability and selectivity, and can be applied to enhance such properties in the enzyme used in the present invention. Directed enzyme evolution is a well known technique, and is reviewed in *Combinatorial Chemistry and High Throughput Screening*, 2006, 9, 247-257. Accordingly, the enzyme used to perform the enantioselective reduction of formula (II), (III) or (IV) may be an enzyme which has undergone directed evolution. It may for instance be an enzyme which has undergone directed evolution from a ketoreductase enzyme, for instance from one of the following specific ketoreductase enzymes: KRED-101, KRED-107, KRED-111, KRED-112, KRED-113, KRED-114, KRED-115, KRED-119, KRED-121, KRED-123, KRED-128, KRED-129, KRED-131, KRED-A1n and KRED-A1x. Alternatively, it may be an enzyme which has undergone directed evolution from an alcohol dehydrogenase enzyme, for instance from ADH-LB or ADH-LK. In one embodiment, the enzyme is one which has undergone directed evolution from ADH-LB.

When the enantioselective reduction of the compound of formula (II), (III) or (IV) is carried out using an enzyme (for instance a ketoreductase or an alcohol dehydrogenase) a hydrogen source is usually also present. The term "hydrogen source", as used herein, means a molecule or a system which provides, overall, a molecule of hydrogen (i.e. two hydrogen atoms) for each ketone group reduced. Thus, in one embodiment, the enantioselective reduction is carried out in the presence of an enzyme and a hydrogen source.

Typically, the hydrogen source comprises either of the two forms of nicotinamide adenine dinucleotide cofactor, NADH or NADPH. These compounds readily oxidise to form $NAD^+$ and $NADP^+$ respectively.

Since NADH and NADPH are not usually available in the amounts necessary to use stoichiometrically, a second reaction is typically employed in order to recycle the oxidised cofactor, $NAD^+$ or $NADP^+$, back to NADH or NADPH respectively. This is known as a cofactor recycling system. Choices for this second reaction are described in *Acc. Chem. Res.* 2007, 40, 1412-1419 and are shown in Scheme 2 below:

Scheme 2
NAD(P)H Cofactor Recycling Systems

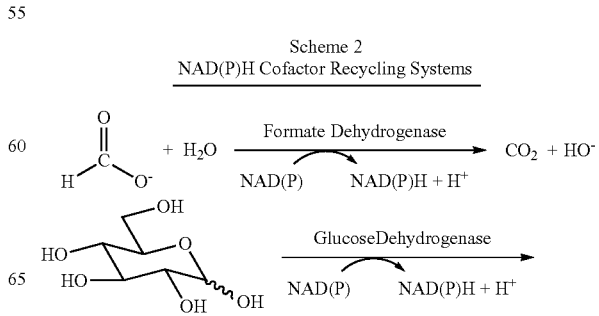

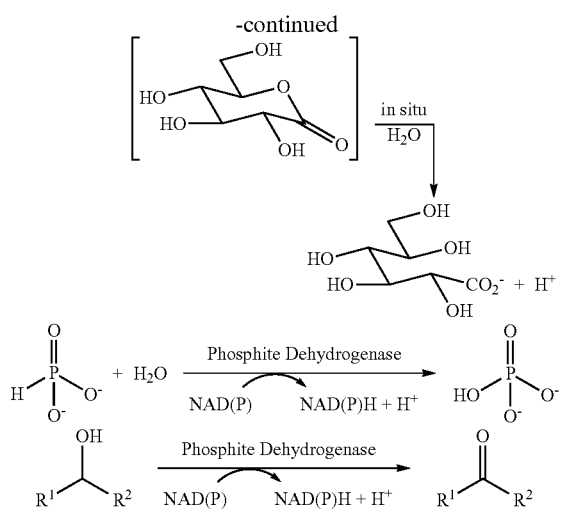

Accordingly, in one embodiment, the enantioselective reduction of the compound of formula (II), (III) or (IV) is carried out using an enzyme (for instance a ketoreductase or an alcohol dehydrogenase) in the presence of:
(a) a hydrogen source selected from NADH and NADPH; and
(b) a NAD(P)H cofactor recycling system.

The NAD(P)H cofactor recycling system usually comprises a cofactor recycling enzyme and a cofactor recycling enzyme substrate. For instance, the NAD(P)H cofactor recycling system may comprise: (i) glucose and glucose dehydrogenase (GDH); (ii) formate and formate dehydrogenase (FDH); (iii) phosphite and phosphite dehydrogenase (PDH); or (iv) a secondary alcohol and a ketoreductase.

Such cofactor recycling enzymes, including GDH, are commercially available. For instance, such cofactor recycling enzymes were available from Biocatalytics, Inc., which is now part of Codexis, Inc.

When a secondary alcohol and a ketoreductase are used as the cofactor recycling enzyme substrate and the cofactor recycling enzyme respectively, as in (iv), the ketoreductase may be the same enzyme as that used to carry out the enantioselective reduction of the compound of formula (II), (III) or (IV).

Usually, the NAD(P)H cofactor recycling system comprises glucose and glucose dehydrogenase (GDH).

Thus, in one embodiment, the enantioselective reduction of formula (II), (III) or (IV) is carried out using the enzyme ADH-LB, in the presence of NADP, GDH and glucose.

Typically, the step of submitting the compound of formula (II), (III) or (IV) to enantioselective reduction is carried out in the presence of a solvent. The solvent used is suitably a polar protic solvent such as water or an alcohol, for instance methanol or ethanol. Usually, the solvent is water.

Usually, the step of submitting the compound of formula (II), (III) or (IV) to enantioselective reduction is carried out in the presence of a buffer. Typically, the buffer is pH neutral. Thus, the pH of the buffer is typically from 6.5 to 7.5, more typically about 7. Any suitable buffer may be used. Typically, however, the buffer is a phosphate buffer or a triethanolamine buffer. More typically, the buffer is a phosphate buffer. The buffer is usually a pH 7 phosphate buffer solution, for instance a 0.2 M pH 7 phosphate buffer solution. These buffer solutions are usually aqueous solutions.

The reaction is typically carried out at or slightly above room temperature, when an enzyme is used to perform the enantioselective reduction. For example, the reaction may be performed at a temperature of from 20° C. to 40° C., more typically from 25° C. to 35° C. Usually, the reaction is performed at about 30° C.

Advantageously, when the pH of the reaction mixture is maintained at a mildly acidic pH the enantioselective reduction of the compound of formula (II), (III) or (IV) may be performed at higher reactant concentrations (for instance at initial concentrations of at least 700 mM of the compound of formula (II), (III) or (IV)) in a single reaction step.

Accordingly, in the process of the invention, the step of submitting the compound of formula (II), (III) or (IV) to enantioselective reduction may be carried out at a mildly acidic pH, for instance at a pH which is less than 7.0 but at least 4.0, more typically at a pH of from 4.5 to 6.5. Even more typically, the step is carried out at a pH of from 5.0 to 6.0. Usually, the pH is maintained in these ranges by the addition of a base during the step of submitting the compound of formula (II), (III) or (IV) to enantioselective reduction. Any suitable base may be employed, for instance a metal hydroxide, a metal carbonate or a metal acetate. Typically, the metal is an alkali metal or an alkaline earth metal. Typically, the base is an alkali metal hydroxide, for instance sodium hydroxide. The base may be added continuously or at discrete intervals during the enantioselective reduction. Typically the base is added as a solution, usually as an aqueous solution of the base. In one embodiment, an aqueous solution of sodium hydroxide is added. Typically, the concentration of the sodium hydroxide solution is from 1 M to 10 M, for instance from 2 M to 7 M, and is more typically about 5 M. Usually the pH is maintained in the range by dropwise addition of the base.

The enantioselective reduction need not be mediated by an enzyme. Rather, in the cases of compounds (II), (III) and (IV), the reduction can alternatively be performed using a chemical reagent suitable for asymmetric reduction.

Thus, in one embodiment, the asymmetric reduction is carried out using a chemical asymmetric reduction process. The term "chemical asymmetric reduction process", as used herein, refers to a process in which asymmetric reduction is mediated by a chemical reagent rather than by an enzyme.

Chemical asymmetric reduction processes and chemical reagents suitable for asymmetric reduction are well known in the art. Such reagents and processes are described, for instance, in the following textbooks: "Asymmetric Catalysis on Industrial Scale", published 2004, Wiley-VCH, editors H. U. Blaser and E. Schmidt; "Strategic Applications of Named Reactions in Organic Synthesis" published 2005, Elsevier, László Kürti and Barbara Czakó; and "Advanced Organic Chemistry, Reactions, Mechanisms and Structure", Jerry March, Fourth Edition, Wiley-Interscience. Furthermore, Angew. Chem. Int. Ed. 2004, 43, 788-824 discusses various methods for the production of enantiomerically pure alcohols.

The enantioselective reduction of the compound of formula (II), (III) or (IV) may for instance be carried out using any one of the following chemical asymmetric reduction processes: (i) asymmetric hydride transfer reduction, (ii) asymmetric hydrogenation, or (iii) asymmetric hydrosilylation followed by silyl ether hydrolysis.

Asymmetric hydride transfer reduction of a ketone can be carried out using an asymmetric hydride transfer reagent, including but not limited to any of the following reagents:
a chiral borane, for instance (R,R)- or (S,S)-2,5-dimethylborolane (H. C. Brown compounds);
LiAlH$_4$ modified with a chiral ligand;
NaBH$_4$ modified with a chiral ligand; or BH$_3$.THF or catecholborane, together with an oxazaborolidine catalyst (Corey-Merck).

*J. Org. Chem.* 1993, 58, 2880 describes a process for preparing a hydro oxazaborole borane for use as an enantioselective catalytic reducing agent. Furthermore, *J. Am. Chem. Soc.* 1992, 144, p1906 gives procedures for oxazaborolidine reduction.

Reduction of a ketone by asymmetric hydrogenation can be carried out using a transition metal hydrogenation catalyst comprising a chiral ligand. Typically, the transition metal is ruthenium. Thus, the catalyst may be a ruthenium complex including a chiral ligand. One notable example of such a catalyst is 2,2'-bis(diphenylphosphino)-1,1'-binaphthyl-ruthenium acetate, [BINAP-Ru(OAc)$_2$]. This hydrogenation catalyst can reduce β-keto esters in >98% ee. Other such asymmetric hydrogenation catalysts include ruthenium hydride complexes which incorporate a chiral ligand, for instance BINAP or a chiral 1,2-diamine ligand.

Rhodium (I) complexes comprising a chiral ligand, e.g. BINAP or a chiral 1,2-diamine ligand, can be used to perform asymmetric hydrosilylation reactions.

After the compound of formula (II), (III) or (IV) has been submitted to enantioselective reduction in order to produce the compound of formula (I), the process of the invention may further comprise: recovering the compound of formula (I).

The term "recovering", as used herein in connection with the compound of formula (I), means isolating the compound in substantially pure form.

Typically, the compound of formula (I) is recovered from a reaction mixture comprising the compound of formula (I). The reaction mixture may comprise the compound of formula (I) and one or more of the following components: a solvent, a buffer, a reactant, a by-product, an enzyme, a hydrogen source, an enzyme cofactor recycling system (e.g. a cofactor recycling enzyme and a cofactor recycling enzyme substrate), a chemical asymmetric reducing reagent and one or more impurities.

In one embodiment, the step of recovering the compound of formula (I) includes extracting the compound of formula (I) into a solvent and recovering the compound of formula (I) from the extract. Typically, the extraction solvent is an organic solvent, more typically a polar organic solvent. More typically, the extraction solvent is a polar aprotic solvent, for instance an ester. Thus, ethyl acetate may be used to extract the compound of formula (I) from the reaction mixture.

More typically, the step of recovering the compound of formula (I) includes extracting the compound of formula (I) in a solvent, drying the resulting extract with a drying agent, and recovering the compound of formula (I) from the extract. Any suitable drying agent may be used, for instance MgSO$_4$. The step of recovering the compound of formula (I) from the extract typically comprises concentrating the extract.

The reaction mixture or the extract may contain one or more impurities in addition to the compound of formula (I), for instance traces of the reactant compound of formula (II), (III) or (IV) and/or one or more reaction by-products.

Accordingly, the step of recovering the compound of formula (I) may comprise purifying the compound of formula (I). Typically, the compound of formula (I) is purified by chromatography, typically column chromatography, for instance silica gel column chromatography.

Thus, in one embodiment, the step of recovering the compound of formula (I) comprises:
extracting the compound of formula (I) in a solvent,
optionally drying the resulting extract with a drying agent,
recovering the compound of formula (I) from the extract, and
purifying the compound of formula (I).

The compound of formula (II) is typically produced from the reaction between 4-hydroxybutan-2-one of formula (V) as defined above and diketene of formula (VI). This diketene route has the advantage that it produces the compound of formula (II) cleanly rather than as part of a complex mixture of products. This reaction is described in the literature, for instance in Lacey, R. N., *J. Chem. Soc.* 1954, 816-822, where chloroform is used as a solvent, and in Miri, R. et al, *DARU* 2002, 10, 130-136, where no solvent is used. Thus, the reaction may be performed in the presence or absence of a solvent. It is typically performed in the presence of heat, for instance at a temperature of at least 40° C., e.g. at about 60° C. The starting materials of formulae (V) and (VI) are commercially available and inexpensive.

Alternatively, the compound of formula (II) may be produced by treating 4-hydroxybutan-2-one of formula (V):

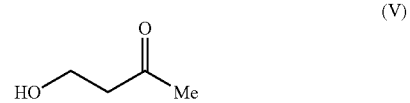

with 2,2,6-trimethyl-4H-1,3-dioxin-4-one of formula (IX):

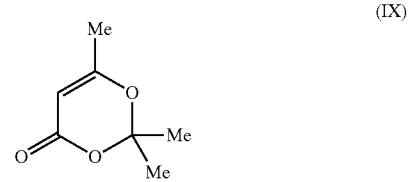

in the presence of a transesterification reagent.

Both 4-hydroxybutan-2-one of formula (V) and 2,2,6-trimethyl-4H-1,3-dioxin-4-one of formula (IX) are commercially available. They can also be prepared from other commercially available starting materials using well-known synthetic procedures.

The transesterification reagent can be an enzymatic or chemical transesterification reagent. Chemical transesterification reagents are well known in the art and include acids and bases, for instance mineral acids, such as sulphuric and hydrochloric acids, sulphonic acids, and bases such as alkali metal hydroxides (for instance sodium or potassium hydroxide) or alkali metal alkoxides. Thus, the transesterification reaction may be a conventional acid- or base-catalysed transesterification. Conventional transesterification reaction conditions may be employed. The reaction may be carried out in the presence or absence of a solvent.

Typically, the by-product of the transesterification reaction between the compounds of formulae (V) and (IX), acetone, is removed during the reaction: in order to drive the equilibrium towards product formation. Typically, the acetone is removed by evaporation, usually under reduced pressure. Usually, the transesterification is carried out at an elevated temperature, for instance at a temperature of from 50 to 150° C.

When an enzymatic transesterification reagent is used, it typically comprises a lipase and may indeed consist only of a lipase. Such lipases are commercially available.

Alternatively, the lipase can be obtained by culturing a suitable micro-organism and subsequently isolating the enzyme. Suitable micro-organisms for this purpose belong to the genuses *Micor, Aspergillus, Rhizopus, Pseudomonas, Candida, Humicola, Thermomyces* and *Penicillum*. In one embodiment, the lipase is from *Candida antarctica*. The enzyme may be unsupported or supported on a solid state carrier.

It should be noted that the enzymatic transesterification usually leads to the formation of a complex mixture of products which then needs to be purified. Usually, therefore, the diketene route is preferred over enzymatic transesterification because the diketene reaction proceeds cleanly to produce the desired product of formula (II).

Enzymatic transesterification typically takes place at a lower temperature than a conventional acid- or base-catalysed transesterification reaction, for instance at a temperature below 100° C. and typically between 20 and 80° C. The enzymatic transesterification reaction may be performed in the presence of absence of a solvent. When a solvent is used, the solvent is chosen to ensure that the reactants have mutual solubility and the activity of the enzymatic transesterification reagent is not impaired.

Suitable solvents for the enzymatic transesterification include alkanes, such as hexane or petroleum ether; aromatic hydrocarbons, such as toluene and benzene; and polar aprotic organic solvents, for instance halogenated hydrocarbons, such as chloroform, carbon tetrachloride and trichloroethane; ethers, such as diethyl ether, diisopropyl ether and dibutyl ether; and ketones, such as methylethylketone, methylpropylketone and diethylketone.

The by-product of the transesterification reaction (in the case of the reaction between compounds (V) and (IX), acetone) is typically removed during the reaction, even when an enzymatic transesterification. reagent is used. Typically, the by-product is removed by evaporation, usually under reduced pressure. The skilled person will understand that the conditions for evaporation will vary depending on the by-product.

The product of the transesterification reaction between compounds (V) and (IX), the compound of formula (II), may be recovered from the reaction mixture and/or purified using conventional techniques.

In another embodiment, the compound of formula (II) is produced by treating 4-hydroxybutan-2-one of formula (V):

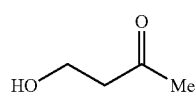

(V)

with a compound of formula (X):

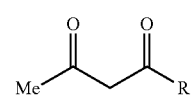

(X)

wherein R is halo or —OR$^1$, wherein R$^1$ is selected from hydrogen, unsubstituted or substituted C$_{1-6}$ alkyl and —C(O)R$^2$ wherein R$^2$ is unsubstituted or substituted C$_{1-6}$ alkyl or -alk-C(O)—R$^3$ wherein alk is unsubstituted or substituted C$_{1-4}$ alkylene and R$^3$ is unsubstituted or substituted C$_{1-4}$ alkyl, in the presence of an esterification reagent when R is —OR$^1$ and R$^1$ is hydrogen, or in the presence of a transesterification reagent when R is —OR$^1$ and R$^1$ is unsubstituted or substituted C$_{1-6}$ alkyl.

A C$_{1-6}$ alkyl group is an unsubstituted or substituted, straight or branched chain, saturated or unsaturated hydrocarbon radical. For example, it may be methyl, ethyl, propyl, butyl, pentyl, hexyl or vinyl. Typically, it is C$_{1-4}$ alkyl, for example methyl, ethyl, iso-propyl, n-propyl, tert-butyl, sec-butyl, iso-butyl, n-butyl or vinyl. In one embodiment, the C$_{1-6}$ or C$_{1-4}$ alkyl group is saturated. Thus, the C$_{1-6}$ alkyl group may be selected from methyl, ethyl, propyl, butyl, pentyl and hexyl, and the C$_{1-4}$ alkyl group may be selected from methyl, ethyl, iso-propyl, n-propyl, tert-butyl, sec-butyl, iso-butyl and n-butyl. When an alkyl group is substituted it typically bears one or more substituents selected from unsubstituted C$_{1-4}$ alkyl, phenyl, phenoxy, nitro, keto, cyano, amino, hydroxy, methoxy, ethoxy, propoxy, butoxy and carboxyl. Typically, a substituted C$_{1-6}$ alkyl group carries 1, 2 or 3 substituents, for instance 1 or 2.

A C$_{1-4}$ alkylene group is an unsubstituted or substituted bidentate moiety obtained by removing two hydrogen atoms, either both from the same carbon atom, or one from each of two different carbon atoms, of a saturated aliphatic hydrocarbon compound having from 1 to 4 carbon atoms (unless otherwise specified). Typically it is, for example methylene, ethylene, i-propylene, n-propylene, t-butylene, i-butylene, s-butylene or n-butylene. An alkylene group may be unsubstituted or substituted, for instance, as specified above for alkyl. Typically a substituted alkylene group carries 1, 2 or 3 substituents, for instance 1 or 2.

As used herein the term halo is a group selected from —F, —Cl, —Br and —I.

Compounds of formula (X) are commercially available or can be prepared from commercially available starting materials using known synthetic procedures. The methyl, ethyl, propyl and butyl acetoacetates are commercially available, as is acetoacetic acid. 4-Hydroxybutan-2-one of formula (V) is also commercially available.

When the compound of formula (X) is an ester (i.e. when R is —OR$^1$ and R$^1$ is substituted or unsubstituted C$_{1-6}$ alkyl), the reaction between (X) and (V) is a transesterification and is carried out in the presence of a transesterification reagent.

The transesterification reagent may be an enzymatic or a chemical transesterification reagent, as described above in connection with the reaction between the compounds of formulae (V) and (IX). The transesterification reaction may be performed under conventional conditions as described previously for the reaction between the compounds of formulae (V) and (IX), and the product (the compound of formula (II)) may be recovered from the reaction mixture and purified using standard techniques.

When the compound formula (X) is acetoacetic acid, the reaction between (X) and (V) is an esterification and is carried out in the presence of an esterification reagent. The esterification reagent may be an enzymatic esterification reagent or a chemical esterification reagent.

The chemical esterification reagent is typically an acid, for instance sulphuric acid or a sulphonic acid, or a base, for instance an alkali metal hydroxide or alkoxide, a metal oxide or a metal alkylatealkoxide. Thus, the esterification may be a conventional acid- or base-catalysed esterification reaction. Conventional reaction conditions for such reactions may be employed. Esterification reactions which employ such acid and base catalysts typically take place at high temperatures, e.g. up to 150° C. Typically, the water produced as a by-product of the esterification reaction is removed during the reaction in order to drive the equilibrium towards product formation. The water may be removed using a dehydrating agent, for instance conc. sulphuric acid, or by evaporation. Other suitable esterification reagents include those that allow water to be removed at room temperature or thereabouts, for instance carbodiimides, e.g. dicyclohexylcarbodiimide (DCC). Further suitable dehydrating agents include: an alkyl chloroformate and Et$_3$N, pyridinium salts-Bu$_3$N, phenyldichlorophosphate (PhOPOCl$_2$), DCC and an aminopyridine, 2-chloro-1,3,5-trinitrobenzene and pyridine, di-2-pyridyl carbonate, polystyryl diphenylphosphine, (trimethylsilyl) ethoxyacetylene, 1,1'-carbonylbis(3-methylimidazolium)triflate (CBMIT), Amberlyst-15, diethyl azodicarboxylate (EtOOCN=NCOOEt) and Ph$_3$P (Mitsunobu esterification reaction), chlorosulfonyl isocyanate (ClSO$_2$NCO), chlorosilanes, MeSO$_2$Cl-Et$_3$N, Ph$_3$P—CCl$_4$-Et$_3$N, N,N'-carbonyldiimidazole, and BF$_3$ etherate (see "Advanced Organic Chemistry, Reactions, Mechanisms and Structure", Jerry March, Fourth Edition, Wiley-Interscience, page 396).

When an enzymatic esterification reagent is used, it typically comprises a lipase, and may consist only of a lipase. Such lipases are commercially available. Alternatively, the lipase can be obtained by culturing a suitable microorganism, as described above in connection with transesterification. In one embodiment, the lipase is from *Candida antarctica*. The enzyme may be unsupported or supported on a carrier (for ease of product purification). As with enzymatic transesterification, enzymatic esterification usually takes place at a lower temperature than a conventional acid- or base-catalysed esterification reaction, for instance at a temperature below 100° C., and typically between 20 and 80° C. The enzymatic esterification reaction may be performed in the presence or absence of a solvent. When a solvent is used, it is chosen to ensure that the reactants have mutual solubility and the activity of the enzymatic esterification reaction is not impaired. Suitable solvents include those listed hereinbefore as solvents suitable for enzymatic transesierification.

The water by-product of the enzymatic esterification reaction can be removed by pervaporation as described in EP 0506159, which describes an enzymatic esterification process.

When the compound formula (X) is an acetoacetyl halide (i.e. when R is halo), the reaction between (X) and (V) is typically carried out in the presence of a base. Any suitable base may be employed; an aqueous alkali, for instance, or pyridine. Conventional reaction conditions (for reactions between an alcohol and an acyl chloride) may be employed.

Typically, when R is halo, R is Cl or Br. More typically, R is Cl.

When R in the compound formula (X) is —OR$^1$ and R$^1$ is —C(O)R$^2$, the reaction between (X) and (V) is typically carried out in the presence of an acid or a base. The acid may be a lewis acid. Any suitable base may be employed; an aqueous alkali, for instance, or pyridine. Conventional reaction conditions (for reactions between an alcohol and an acid anhydride) may be employed.

Typically, when R in the compound formula (X) is —OR$^1$ and R$^1$ is —C(O)R$^2$, R$^2$ is -alk-C(O)—R$^3$. Typically, alk is —CH$_2$—. Typically, R$^3$ is methyl. Thus, typically, in this embodiment, the compound of formula (X) is acetoacetic anhydride.

The product of the esterification process, the compound of formula (II), may be recovered from the reaction mixture and/or purified using conventional techniques.

The compound of formula (III) is typically produced from the reaction between (R)-1,3-butanediol of formula (VII) and diketene of formula (VI). There is a reference in the literature to this reaction, that uses the corresponding racemic butanediol; this is Desrochers, S. et al, *Nutritional Biochemistry* 1995, 6, pp 111-118. In addition, the compound of formula (III) is described in GB 1172419, being one of a number of 'polyester accelerators' that 'can be easily obtained, for example by reacting diketene with the appropriate alcohols.' The diol of formula (VII) is commercially-available.

Alternatively, the compound of formula (III) may be produced by treating (R)-1,3-butanediol of formula (VII):

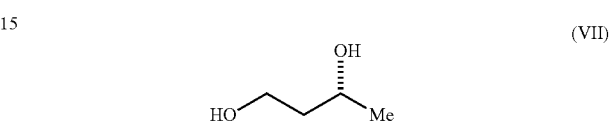

(VII)

with 2,2,6-trimethyl-4H-1,3 dioxin-4-one of formula (IX):

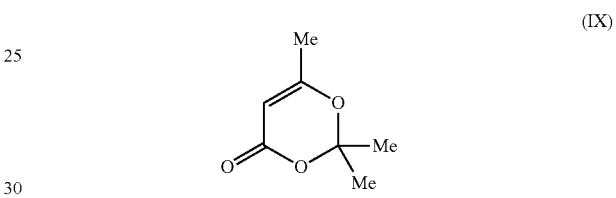

(IX)

in the presence of a transesterification reagent.

The compounds of formulae (VII) and (IX) are both commercially available. They can also be prepared from other commercially available starting materials using conventional synthetic procedures. The transesterification reaction between the compounds of formulae (VII) and (IX) can be carried out under conventional reaction conditions, using either an enzymatic transesterification reagent or a chemical (non-enzymatic) transesterification reagent, as described above in relation to the reactions between the compounds of formulae (V) and (IX). The product compound of formula (III) may be recovered from the reaction mixture and/or purified using conventional techniques.

In another embodiment, the compound of formula (III) is produced by treating (R)-1,3-butanediol of formula (VII):

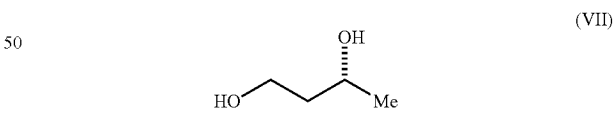

(VII)

with a compound of formula (X):

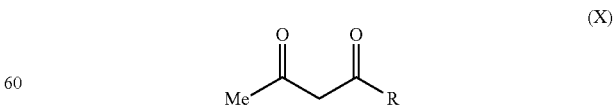

(X)

wherein R is halo or —OR$^1$, wherein R$^1$ is selected from hydrogen, unsubstituted or substituted C$_{1-6}$ alkyl and —C(O)R$^2$ wherein R$^2$ is unsubstituted or substituted C$_{1-6}$ alkyl or -alk-C(O)—R$^3$ wherein alk is unsubstituted or substituted C$_1$ alkylene and R$^3$ is unsubstituted or substituted C$_{1-4}$ alkyl, in the presence of an esterification reagent when R is —OR[1] and R[1] is hydrogen, or in the presence of a transesterification reagent when R is —OR[1] and R[1] is unsubstituted or substituted $C_{1-6}$ alkyl.

The reaction between the compounds of formulae (VII) and (X) can be carried out under conventional reaction conditions, using either an enzymatic or a chemical (non-enzymatic) reagent, as described above in relation to the reactions between the compounds of formulae (V) and (X). The product compound of formula (III) may be recovered from the reaction mixture and/or purified using conventional techniques.

The compound of formula (IV) is typically produced from the reaction between 4-hydroxybutan-2-one of formula (V), as defined above, and (R)-4-methyloxetan-2-one of formula (VIII). This reaction can be carried out under conventional esterification conditions, for instance under the conditions described above in relation to the esterification reaction between the compounds of formulae (V) and (X). The 4-hydroxybutan-2-one of formula (V) is treated with (R)-4-methyloxetan-2-one of formula (VIII) and the reaction mixture may be heated, if necessary. The reaction can be carried out in the absence or presence of a solvent, and is usually performed in the presence of an esterification reagent, as defined above, for instance in the presence of a catalytic amount of an acid. The product compound of formula (IV) may be recovered from the reaction mixture and/or purified using conventional techniques.

The compound of formula (V), 4-hydroxybutan-2-one is commercially available and inexpensive. The other reactant, (R)-4-rnethyloxetan-2-one, can be produced by known methods which are described in the literature, for instance by cyclisation of methyl (S)-3-bromobutyrate; asymmetric hydrogenation of diketene (*J. Chem. Soc. Chem. Conimun.* 1992, 1725-1726, Ohta et al.); resolution of the racemate of 4-methyloxetan-2-one using a lipase (*J. Chem. Soc. Perkin Trans.* 1, 2000, 71-77, Sakai et al.); carbonylation of (R)-propylene oxide (*Acc. Chem. Res.* 1995, 28, 414); and catalytic asymmetric condensation of acetyl bromide and acetaldehyde.

The (3R)-hydroxybutyl(3R)-hydroxybutyrate produced by the process of the invention is typically produced as an enantiomercially enriched sample of 3-hydroxybutyl 3-hydroxybutyrate comprising at least 96% of the (3R,3'R) enantiomer. It may comprise at least 97%, for example at least 98%, or at least 99%, of the (3R,3'R) enantiomer.

The (3R)-hydroxybutyl(3R)-hydroxybutyrate produced by the process of the invention may be included in a food product. A food product is an edible material composed primarily of one or more of the macronutrients protein, carbohydrate and fat. A food product may also contain one or more micronutrients such as vitamins or minerals, or additional dietary ingredients such as flavourants and colourants. The (3R)-hydroxybutyl(3R)-hydroxybutyrate may be formulated into a food product, for instance by mixing with the constituent macronutrients and/or micronutrients of that product. The invention will be further described in the Examples which follow:

EXAMPLE 1

Enzymatic Reduction of 3-oxobutyl acetoacetate

1. Enzyme Activity Screening

A range of alcohol dehydrogenases was screened for activity toward 3-oxobutyl acetoacetete, formula (II), by monitoring cofactor consumption at 340 nm over time (Table 1). The enzymes screened were ADH from *Lactobacillus brevis* (ADH-LB), ADH 1 and 2 from *Rhodococcus* sp. (ADH-RS1 and ADH-RS2), ADH from. *Thermoanaerobacter* sp. (ADH-T) and ADH 1 and 2 from *Lactobacillus kefir* (CDX 003 and CDX 013 respectively).

TABLE 1

Spectrophotometric screening of various ADHs for activity toward 3-oxobutyl acetoacetate

| Alcohol dehydrogenase | Activity | Relative activity[1] |
| --- | --- | --- |
| ADH-LB | 825 U/mL | 114% |
| ADH-RS1 | 471 U/mL | 170% |
| ADH-RS2 | 90 U/mL | 170% |
| ADH-T | 157 U/mL | 10% |
| CDX 003 | 9 U/mg | 28% |
| CDX 013 | <0.1 U/mg | — |

[1]Activity relative to standard substrate

The highest activities were obtained with ADH LB and ADH RS1. These two enzymes were selected from studying the bioreductions on analytical scale.

2. Bioreduction of 3-oxobutyl acetoacetate by ADH LB and ADH RS1

The formula (II) substrate 3-oxobutyl acetoacetate (1 mL, 60 mM) was incubated overnight with the alcohol dehydrogenases ADH RS1 or ADH LB (10 U/mL) and glucose dehydrogenase (10 U/mL) for co-factor regeneration. After derivatisation of the products to form the bis(trifluoroacetate) esters thereof, the samples were analysed by chiral gas chromatography. The analyses revealed that ADH-LB gave (3R)-hydroxybutyl(3R)-hydroxybutyrate in greater than 99.8% ee, whereas ADH-RS1 gave the (3S,3'S) isomer in greater than 99.6% ee; ADH-RS 1 is an S-selective enzyme whereas ADH-LB is an R-selective enzyme.

3. Asymmetric Reduction of 3-oxobutyl acetoacetate (II) by ADH-LB, GDH, NADP Biocatalytic System The reactions were carried out in phosphate 0.2 M buffer at 30° C. open to air. The progress of the reactions was followed by TLC and NMR analysis. Most of the reactions were completed within 6 to 8 h according to TLC, but usually were left stirring overnight. Usual loading of enzymes & co-factor were as follows: 40 mg (3 kU) of GDH, 47 mg (0.06 mmol) of β-NADP per 0.6 mL (suspension, 2.9 kU) of ADH-LB.

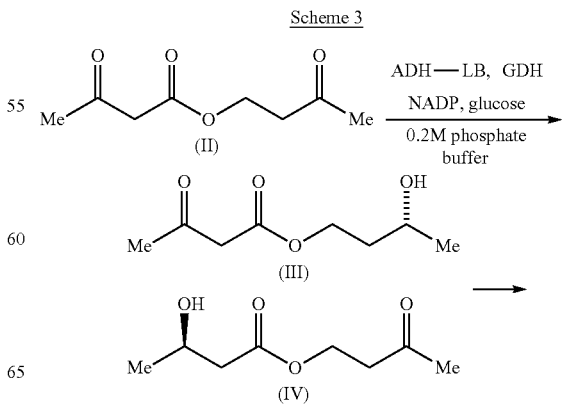

Scheme 3

-continued

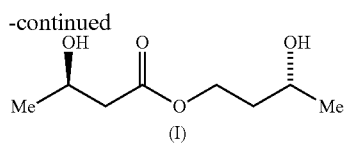

Analysis of the crude product by $^1$H NMR allowed estimation of the level of reduction of the keto-units of (II), which is presented by 'conversion' in the following Table 2:

TABLE 2

Asymmetric reductions of (II)

| [(II)], mM | Mass (II), g. | Mol equiv. glucose | ADH-LB kU | Time, h | Conversion |
|---|---|---|---|---|---|
| 200 | 1.92 | 3 | 2.9 | 18 | Quant. |
| 220 | 5.0 | 3 | 2.9 | 18 | Quant. |
| 250 | 5.8 | 2.5 | 5.8 | 18 | 80% |
| 250 | 5.8 | 3 | 2.9 | 18 | 90% |
| 300-350 | 5.8 | 3 | 5.8 | 18 | 80% |
| 700 | 5.8 | 3→4 | 2.9 | 48 | 60% |
| 700 | 5.8 | 3 | 5.8 | 24 | 60% |
| 700 | 4.73 | 1.5 | 2.9 | 18 | 60% |
| 700 product of 60% conv | 5.2 | 1.5 | 2.9 | 18 | Quant. |

As the table shows, quantitative ketone reduction could be achieved in a single-batch reaction with 220 mM concentration of the diketone of formula (II) and 3 equivalents of glucose. Higher concentrations (250-350 mM) proceeded to lower conversion and at 700 mM a two-step reduction was required for quantitative conversion.

Experimental Procedure for the 220 mM Reaction:

To a solution of diketone 2 (5.0 g, 29.1 mmol) and glucose monohydrate (17.3 g, 87.2 mmol) in 0.2 M phosphate buffer (132 mL) was added ADH-LB (2.9 kU, 0.6 mL), GDH (3 kU, 40 mg) and β-NADP (47 mg, 0.06 mmol). The resulting mixture was stirred at 30° C. for 18 h. Formation of a white precipitate/gel led to 'milkiness' of the solution. TLC analysis indicated full conversion of the starting material and quantitative formation of the monoester (I). The reaction mixture was concentrated with ammonium sulfate and extracted with ethyl acetate (4×125 mL). The combined organic solutions were dried and evaporated to give the crude product (I) (3.86 g, 76%), an aliquot of which was further purified by flash column chromatography (ethyl acetate/petrol, 4:1) for analysis.

It was clear from the results presented in Table 2 that there were two areas for development:
(i) scaleability; the reactions in Table 2 were done in dilute solutions (e.g. 1.9 g in 60 mL buffer) whereas such concentrations are not appropriate for bulk production; (ii) yield; the presence of by-products led to low isolated yields of (I). Thus, process development work was carried out in order to improve both the yield and concentration. In particular, pH control was investigated.

4. Process Development: Onvestigation of pH Control

During the 700 mM reaction (6$^{th}$ entry, Table 2) the pH dropped from 7.5 in the original reaction mixture to approximately pH 5.0 over the first two hours of reaction. Addition of a 1 M sodium hydroxide solution maintained the pH in the region of 7.0-8.0; the last portion of base was added after 8 h and no further pH change was observed on stirring the reaction for a further 12 h. The reaction was worked up according to the above procedure for 220 mM concentration, giving a ca. 50% mass balance of impure product (I). During a similar reaction (5.2 g of diketone in 42 mL of phosphate buffer and 49 kU of ADH-LB) the mixture was further diluted with 63 mL of saturated aqueous disodium hydrogen phosphate added over 8 h. The final pH was ca. 7.5; this did not change on stirring the reaction for a further 1.2 h. On this occasion, standard work-up gave a ca. 90% mass balance of product consisting almost entirely of the monoeter (I). The final reaction volume was 105 mL (290 mM for 5.2 g of diketone). From these observations it was concluded that in order to perform ADH-LB reductions at higher concentrations of diketone, a 7.5 pH buffer with a higher 'basic capacity' would be necessary.

Investigations into Rough Control of pH

Following the conclusions of the previous section, 0.4 M, 0.5 M and 0.7 M phosphate pH 7.5 buffers were employed and it was noted that reactions performed in these buffers led to lower extractions of organic products from the aqueous reaction mixtures and multiple products formed arising from decomposition of diketone (II). From this it was concluded that the starting material was unstable under basic conditions. In borate buffers the reaction appeared to proceed until the pH reached a level of around 3.0 (indicator paper). From this it was concluded that the reaction could be carried out at a mildly acidic pH, with less decomposition of the reactant. In general, reactions in borate buffer were noted to be 'cleaner' but provided lower conversions then those carried out in 0.2 M phosphate buffer. 0.5 M Triethanolamine buffer was found to give the highest level of keto-group reductions, although formation of unwanted by-products was significant in this case. The use of 1 M triethanolamine buffer led to considerable decomposition of the starting material.

Finer Control of pH

Further reactions were started in 0.2 M pH 7.0 phosphate buffer (prepared by mixing 0.2 M Na$_2$HPO$_4$ solution with 0.2 M NaH$_2$PO$_4$ solution until the desired pH was obtained) and pH was constantly monitored (pH meter) and maintained in the range 5.0-6.0 using very slow dropwise additions of 5 M. aqueous sodium hydroxide (Scheme 4, Table 3).

Scheme 4

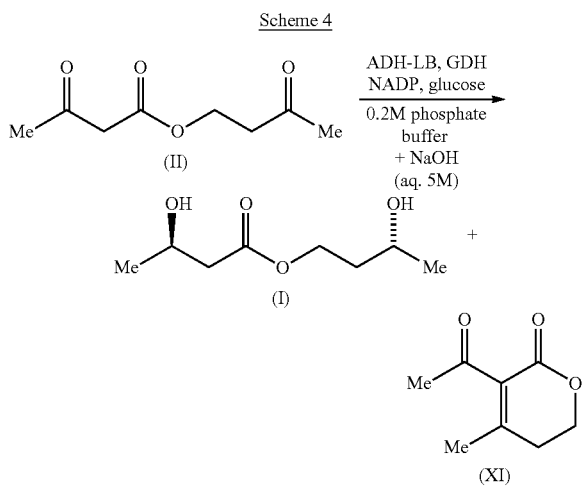

Reactions were carried out consecutively decreasing the volume of buffer used. The crude yields represent mixtures of monoester (I) and the major by-product (XI) (approx. 5% by NMR analysis of crude product).

TABLE 3

Asymmetric reductions of (III) using pH control

| [(II)], mM | Mass (II), g | Volume buffer, mL | Volume of 5M NaOH, mL | ADH-LB kU | Time, h | Crude yield, % |
|---|---|---|---|---|---|---|
| 400 | 4.0 | 58 | 8.2 | 1.45 | 8 | 80 |
| 500 | 4.0 | 47 | 8.1 | 1.45 | 8 | 78 |
| 700 | 4.0 | 33 | 8.1 | 1.45 | 8 | 74 |
| 1000 | 4.0 | 24 | 8.0 | 1.45 | 8 | 76 |
| 1000 | 12.1 | 71 | 21 | 4.35 | 8 | 71* |

*Yield of monoester after column chromatography

An automated addition of aqueous base over the reaction time can be developed.

The structure of the by-product (XI) was established after column chromatography of the 12.1 g scale reaction. The lactone (XI) is formed by base-catalysed aldol cyclisation of the startin material (II). This compound has a very similar polarity to the monoester (I), but was found to be easily separable by GC (indicating easy separation by distillation).

5. Experimental Procedure for Preparative Scale Reaction: Synthesis of (3R)-hydroxybutyl(3R)-hydroxybutyrate To a solution of diketone of formula (II) (12.1 g, 70.3 mmol) and D-glucose (41.8 g, 232 mmol) in 0.2 M phosphate buffer (pH 7.0, 71 mL) was added successively NADP (94 mg), glucose dehydrogenase (GDH, 75 U mg$^{-1}$, 80 mg, 6 kU), and alcohol dehydrogenase from *Lactobacillus brevis* (ADH-LB, aq. suspension, 4.8 kU mL$^{-1}$, 0.91 mL, 4.37 kU). The mixture was stirred for 8 hours at 30° C. and the pH was monitored, adding aqueous NaOH solution (5 M, 21.0 mL, 105 mmol) dropwise in order to maintain a reaction pH between 5.0 and 6.0 (Caution! The base should be added as slowly as possible to avoid decomposition or base-catalysed reactions of the starting material). The organic products were extracted into ethyl acetate (5×120 mL) and the combined extracts were dried (MgSO$_4$) and concentrated in vacua to give the crude product (9.6 g, 78%) which was purified by flash column chromatography (silica gel; ethyl acetate/petrol, 4:1) to give the (3R)-hydroxybutyl(3R)-hydroxybutyrate of formula (I) (8.8 g, 71%). [α]$_D^{23}$ −47.1 (c 1.0, CHCl$_3$); δ$_H$ (400 MHz, CDCl$_3$) 1.15-1.20 (6 H, m, 2×CH$_3$), 1.65-1.80 (2 H, m, CH$_2$CH$_2$O—), 2.35-2.50 (2 H, m, CH$_2$CO—), 3.00-3.30 (1 H, br, 2×OH), 3.80-3.90 (1 H, m, C$_2$H$_4$CHOH), 4.10-4.20 (2 H, m) and 4.25-4.35 (1 H, m, CH(OH)CH$_2$CO— and CH$_2$OCO—); δ$_C$ (100 MHz, CDCl$_3$) 22.6 (CH$_3$), 23.5 (CH$_3$), 37.6 (CH$_2$), 43.2 (CH$_2$), 62.1 (CH$_2$), 64.3 (CH), 64.9 (CH), 172.9 (C=O).

EXAMPLE 2

Production of 3-oxobutyl acetoacetate (II) from Diketene and 4-hydroxybutan-2-one A solution of 4-hydroxybutan-2-one (8.6 mL, 100 mmol) and triethylamine (55 μL, 0.004 equiv.) in chloroform (25 mL) was heated to 60° C. Diketene (8.1 mL, 1.05 equiv.) was added dropwise [CARE: there is a short induction period] and the reaction was stirred at this temperature for a further 45 min by which time NMR analysis indicated the reaction to be complete. The solvent was removed in vacuo and the residue was distilled (Kugelrohr, ca. 0.5 mm Hg, oven temperature 120° C. to remove a short fore-run then the product distilled when the oven temperature was raised to 160° C.) to give the pure product (II) as a colourless oil (13.2 g, 77%). δ$_H$ (200 MHz, CDCl$_3$) 2.19 (3 H, s) and 2.25 (3 H, s, 2×CH$_3$), 2.80 (2 H, t, J 6.2 Hz, CH$_2$CO), 3.44 (2 H, s, CH$_2$(CO)$_2$), 4.40 (2 H, t, J 6.2 Hz, CH$_2$O) [resonances due to the minor enol tautomer were observed at 1.92 and 4.95 p.p.m.].

The invention claimed is:

1. A process for producing (3R)-hydroxybutyl (3R)-hydroxybutyrate of formula (I):

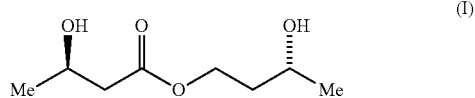 [SMILES: C[C@@H](O)CCOC(=O)C[C@@H](C)O]

(I)

which process comprises submitting, to enantioselective reduction, a compound of the following formula (II), (III) or (IV):

(II)

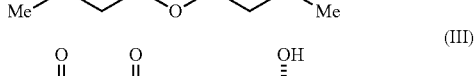

(III)

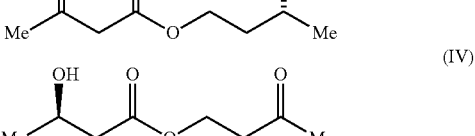

(IV)

2. A process according to claim 1 which further comprises producing the compound of formula (II) by treating 4-hydroxybutan-2-one of formula (V):

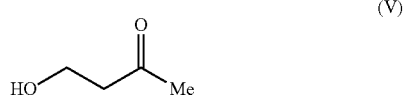

(V)

with diketene of formula (VI):

(VI)

3. A process according to claim 1 which further comprises producing the compound of formula (II) by treating 4-hydroxybutan-2-one of formula (V):

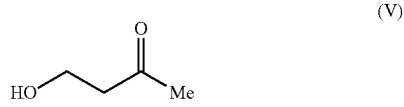

(V)

with 2,2,6-trimethyl-4H-1,3-dioxin-4-one of formula (IX):

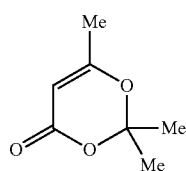
(IX)

in the presence of a transesterification reagent.

4. A process according to claim 1, which further comprises producing the compound of formula (II) by treating 4-hydroxybutan-2-one of formula (V):

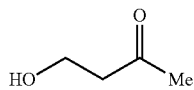
(V)

with a compound of formula (X):

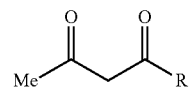
(X)

wherein R is halo or —OR¹, wherein R¹ is selected from hydrogen, unsubstituted or substituted $C_{1-6}$ alkyl and —C(O)R², wherein R² is unsubstituted or substituted $C_{1-6}$ alkyl or -alk-C(O)—R³, wherein alk is unsubstituted or substituted $C_{1-4}$ alkylene and R³ is unsubstituted or substituted $C_{1-4}$ alkyl, in the presence of an esterification reagent when R is —OR¹ and R¹ is hydrogen, or in the presence of a transesterification reagent when R is —OR¹ and R¹ is unsubstituted or substituted $C_{1-6}$ alkyl.

5. A process according to claim 1 which further comprises producing the compound of formula (III) by treating (R)-1,3-butanediol of formula (VII):

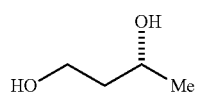
(VII)

with diketene of formula (VI):

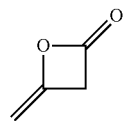
(VI)

and isolating the compound of formula (III) from the resulting mixture of acylated products.

6. A process according to claim 1 which further comprises producing the compound of formula (III) by treating (R)-1,3-butanediol of formula (VII):

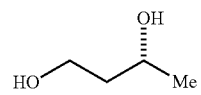
(VII)

with 2,2,6-trimethyl-4H-1,3-dioxin-4-one of formula (IX):

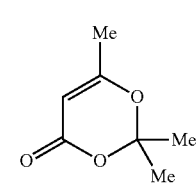
(IX)

in the presence of a transesterification reagent.

7. A process according to claim 1 which further comprises producing the compound of formula (III) by treating (R)-1,3-butanediol of formula (VII):

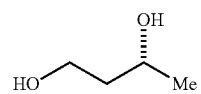
(VII)

with a compound of formula (X):

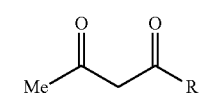
(X)

wherein R is halo or —OR, wherein R¹ is selected from hydrogen, unsubstituted or substituted $C_{1-6}$ alkyl and —C(O)R², wherein R² is unsubstituted or substituted $C_{1-6}$ alkyl or -alk-C(O)—R³, wherein alk is unsubstituted or substituted $C_{1-4}$ alkylene and R³ is unsubstituted or substituted $C_{1-4}$ alkyl, in the presence of an esterification reagent when R is —OR and R¹ is hydrogen, or in the presence of a transesterification reagent when R is —OR and R¹ is unsubstituted or substituted $C_{1-6}$ alkyl.

8. A process according to claim 1 which further comprises producing the compound of formula (IV) by treating 4-hydroxybutan-2-one of formula (V):

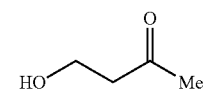
(V)

with (R)-4-methyloxetan-2-one of formula (VIII):

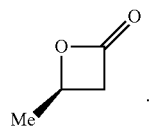
(VIII)

9. A process according to claim 1 wherein the enantioselective reduction is carried out using an enzyme.

10. A process according to claim 9 wherein the enzyme is a ketoreductase (KRED) or an alcohol dehydrogenase (ADH).

11. A process according to claim 9 wherein the enzyme is the alcohol dehydrogenase from *Lactobacillus brevis* (ADH-LB).

12. A process according to claim 9 wherein the step of submitting the compound of formula (II), (Ill) or (IV) to enantioselective reduction is carried out at a pH which is less than 7.0 but at least 4.0.

13. A process according to claim 9 wherein the step of submitting the compound of formula (II), (Ill) or (IV) to enantioselective reduction is carried out at a pH of from 5.0 to 6.0.

14. A process according to claim 1 wherein the enantioselective reduction is carried out using a chemical asymmetric reduction process.

15. A process for producing (3R)-hydroxybutyl (3R)-hydroxybutyrate of formula (I):

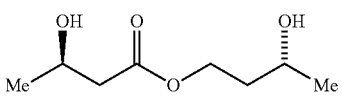
(I)

which process comprises:
(a) treating 4-hydroxbutan-2-one of formula (V):

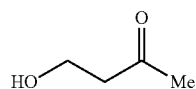
(V)

with diketene of formula (VI):

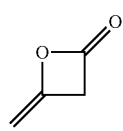
(VI)

to produce a compound of formula (II):

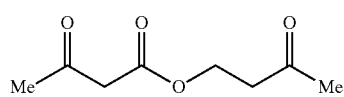
(II)

and
(b) submitting the compound of formula (II) to enantioselective reduction.

16. A process for producing (3-R) -hydroxybutyl (3-R)-hydroxybutyrate of formula (I):

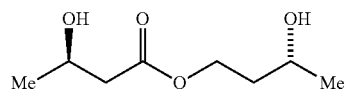
(I)

which process comprises:
(a) treating (R)-1,3-butanediol of formula (VII):

(VII)

with diketene of formula (VI):

(VI)

and isolating a compound formula (III) from the resulting mixture of acylated products:

(III)

and
(b) submitting the compound of formula (III) to enantioselective reduction.

17. A process for producing (3-R-)hydroxybutyl (3J[yen])-hydroxybutyrate of formula (I):

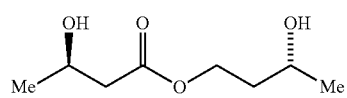
(I)

which process comprises:
(a) treating 4-hydroxybutan-2-one of formula (V):

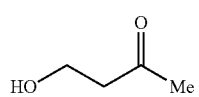
(V)

with (R)-4-methyloxetan-2-one of formula (VIII):
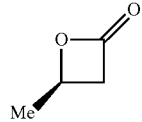
(VIII)
to produce a compound of formula (IV):
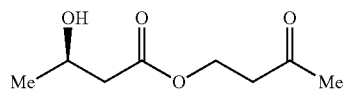
(IV)
and
(b) submitting the compound of formula (IV) to enantioselective reduction.
* * * * *

UNITED STATES PATENT AND TRADEMARK OFFICE
CERTIFICATE OF CORRECTION

| | | |
|---|---|---|
| PATENT NO. | : 9,034,613 B2 | Page 1 of 1 |
| APPLICATION NO. | : 13/264533 | |
| DATED | : May 19, 2015 | |
| INVENTOR(S) | : Jeremy Robertson et al. | |

It is certified that error appears in the above-identified patent and that said Letters Patent is hereby corrected as shown below:

Title Page, item (73), Please correct a clerical error in the address of the Assignee on the cover page of the patent by replacing -- ISIS Innovation Limited, Rockville, Maryland -- with -- ISIS Innovation Limited, Oxford, United Kingdom --

Signed and Sealed this
Sixth Day of October, 2015

Michelle K. Lee
*Director of the United States Patent and Trademark Office*